US010478302B2

(12) United States Patent
Seguin et al.

(10) Patent No.: US 10,478,302 B2
(45) Date of Patent: *Nov. 19, 2019

(54) MATERIAL FOR TREATMENT OF A HEART VALVE, IN PARTICULAR A MITRAL VALVE

(71) Applicant: MEDTRONIC CV LUXEMBOURG S.A.R.L., Luxembourg (LU)

(72) Inventors: Jacques R. Seguin, Windsor (GB); Bruno Lecointe, Var (FR)

(73) Assignee: MEDTRONIC CV LUXEMBOURG S.A.R.L., Luxembourg (LU)

( * ) Notice: Subject to any disclaimer, the term of this patent is extended or adjusted under 35 U.S.C. 154(b) by 416 days.

This patent is subject to a terminal disclaimer.

(21) Appl. No.: 14/960,474

(22) Filed: Dec. 7, 2015

(65) Prior Publication Data

US 2016/0151156 A1    Jun. 2, 2016

Related U.S. Application Data

(63) Continuation of application No. 12/519,498, filed as application No. PCT/IB2007/003975 on Dec. 18, 2007, now Pat. No. 9,232,942.

(Continued)

(30) Foreign Application Priority Data

Dec. 22, 2006    (FR) ..................................... 06 11284

(51) Int. Cl.
*A61F 2/24*    (2006.01)
*A61B 17/068*    (2006.01)
(Continued)

(52) U.S. Cl.
CPC .......... *A61F 2/2445* (2013.01); *A61B 17/068* (2013.01); *A61F 2/2427* (2013.01);
(Continued)

(58) Field of Classification Search
CPC .................. A61F 2/2445; A61F 2/2427; A61F 2210/0014
(Continued)

(56) References Cited

U.S. PATENT DOCUMENTS 6,371,979 B1    4/2002    Beyar et al.
7,491,232 B2    2/2009    Bolduc et al.
(Continued)

FOREIGN PATENT DOCUMENTS

WO    WO200203892    1/2002
WO    WO2004103223    12/2004
(Continued)

*Primary Examiner* — Vy Bui
(74) *Attorney, Agent, or Firm* — Medler Ferro Woodhouse & Mills PLLC

(57) ABSTRACT

This material comprises an annuloplasty member able to be introduced using a catheter through minimally invasive vascular access, then to be delivered by said catheter and fixed to the valve annulus. According to the invention, it includes at least one catheter comprising at least one guide member able to be deployed from said catheter such that it extends along one portion of the valve annulus of the valve, in the immediate proximity of said valve annulus, and an implant having a helical shape engaged on said guide member, connected, with separation possibility, to actuation means making it possible to cause this implant to move forward while driving it in rotation around its axis; the implant can thus be deployed from the catheter while being simultaneously moved forward and driven in rotation along its axis.

20 Claims, 7 Drawing Sheets

Related U.S. Application Data

(60) Provisional application No. 60/876,547, filed on Dec. 22, 2006.

(51) Int. Cl.
  *A61B 17/00* (2006.01)
  *A61B 17/064* (2006.01)
  *A61B 17/22* (2006.01)

(52) U.S. Cl.
  CPC .............. *A61B 2017/00243* (2013.01); *A61B 2017/00292* (2013.01); *A61B 2017/00783* (2013.01); *A61B 2017/00867* (2013.01); *A61B 2017/0649* (2013.01); *A61B 2017/22038* (2013.01); *A61F 2210/0014* (2013.01)

(58) Field of Classification Search
  USPC ................ 606/41, 142, 144, 108, 153, 185; 623/1.11, 1.15, 1.34, 1.36, 13.14
  See application file for complete search history.

(56) References Cited

U.S. PATENT DOCUMENTS

| | | |
|---|---|---|
| 7,887,476 B2 | 2/2011 | Hermann |
| 2004/0049211 A1 | 3/2004 | Tremuis et al. |
| 2005/0251201 A1* | 11/2005 | Roue .................. A61B 17/0057 606/213 |
| 2006/0030885 A1 | 2/2006 | Hyde |
| 2007/0118151 A1 | 5/2007 | Davidson |

FOREIGN PATENT DOCUMENTS

| | | |
|---|---|---|
| WO | WO2005087139 | 9/2005 |
| WO | WO2006091163 | 8/2006 |

* cited by examiner

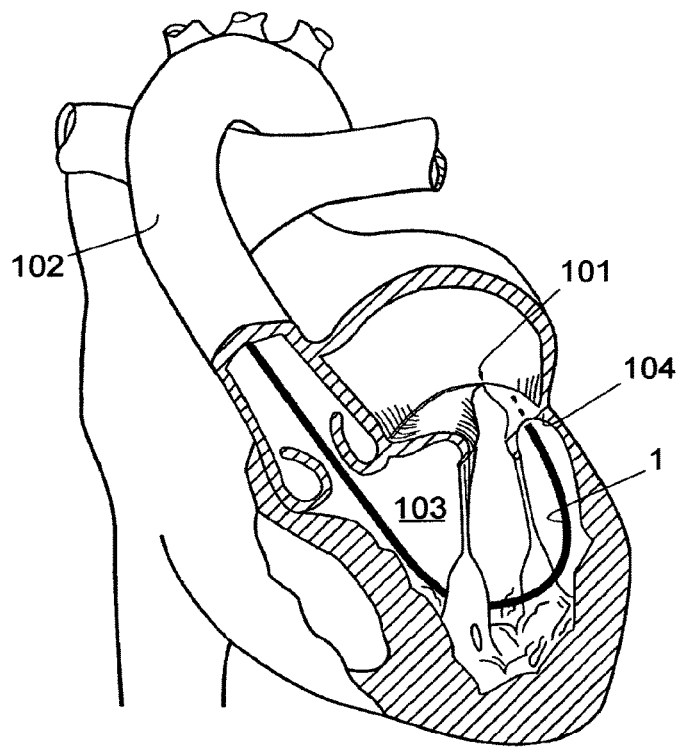
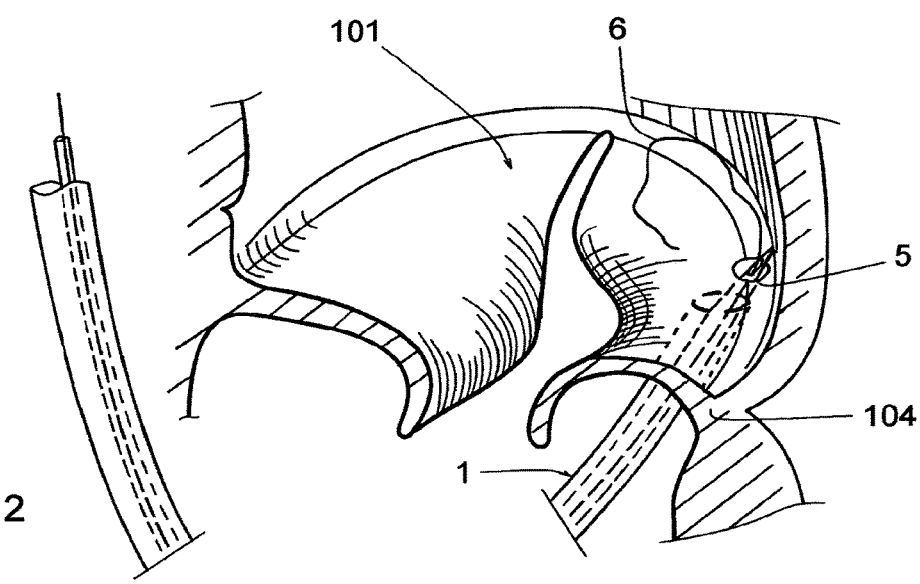
FIG. 1
FIG. 2

MATERIAL FOR TREATMENT OF A HEART VALVE, IN PARTICULAR A MITRAL VALVE

CROSS-REFERENCE TO RELATED APPLICATION

This application is a continuation of U.S. application Ser. No. 12/519,498 filed Jan. 22, 2010, which is a national phase application under 35 U.S.C. § 371 of PCT/IB2007/003975 filed Dec. 18, 2007, which claims the benefit of U.S. Appl. No. 60/876,547 filed Dec. 22, 2006 and which claims foreign priority to FR 06 11284 filed Dec. 22, 2006, the disclosures of which are incorporated by reference herein in their entirety.

FIELD OF THE INVENTION

The present invention relates to a material for treating a heart valve, in particular a mitral valve of a heart. This treatment may consist of performing an annuloplasty, i.e. decreasing distention of the annulus, or of strengthening the annulus of a normal valve. The invention also relates to a percutaneous method for performing a treatment of this type.

BACKGROUND OF THE INVENTION

The annulus of a heart valve may, over time, be subject to distention leading to poor coaptation of the leaflets, resulting in decreased sealing of the valve.

To treat this ailment, it is well-known to perform an annuloplasty, i.e. a recalibration of the annulus using a member implanted on the valve annulus.

This annuloplasty member may be a prosthetic annulus fixed on the native valve annulus. This technique, however, has the drawback of involving open-heart surgery.

The annuloplasty member may also be a deformable member, able to be introduced using a catheter through minimally-invasive vascular access, then able to be delivered through the catheter and fixed near the valve annulus before being circumferentially withdrawn.

The existing annuloplasty members of this type, and the corresponding implantation techniques, like systems using the coronary sinuses, are not, however, fully satisfactory.

Moreover, it may be necessary to implant a prosthetic heart valve, in particular percutaneously using a catheter. Currently, this type of percutaneous implantation is difficult on the mitral valve of a heart, due essentially to the fact that the annulus of a mitral valve is elastic and may be distended during percutaneous implantation of a prosthetic valve.

BRIEF SUMMARY OF THE INVENTION

The present invention essentially aims to resolve the drawbacks and gaps of the earlier techniques.

The concerned material comprises, in a known manner, an annuloplasty member able to be introduced using a catheter through minimally invasive vascular access, then to be delivered by said catheter and fixed to the valve annulus.

According to the invention, the material includes at least one catheter, comprising at least one guide member able to be deployed from said catheter such that it extends along one portion of the valve annulus of the valve, in the immediate proximity of said valve annulus, and an implant having a helical shape engaged on said guide member, connected, with separation possibility, to actuation means making it possible to cause this implant to move forward while driving it in rotation around its axis; the implant can thus be deployed from the catheter while being simultaneously moved forward and driven in rotation along its axis, said rotation enabling the implant to penetrate the tissue of the valve annulus while being guided along said annulus by said guide member.

The material according to the invention thus allows the implant to be placed very precisely along a segment of the valve annulus, using minimally-invasive access. The guide member is retracted into the catheter after placement of the implant, only the latter part remaining in place at the valve annulus.

The implant may vary in length and can adopt an extended shape for introduction and a shortened shape for implantation, the passage of the implant to this shortened implantation shape making it possible to gather the valve annulus portion in which said implant is placed.

In this case, the implant allows performance of an annuloplasty.

For passage of the implant from its extended shape to its shortened shape, said implant is preferably made of a shape memory material. This implant may in particular be in a nickel and titanium alloy known by the name "nitinol".

The implant can also have an invariable or slightly variable length. The implant can then be used to prevent distention of the valve annulus portion in which it is implanted, and/or to form a stiff annular or semi-annular frame, making it possible to implant and anchor a prosthetic valve percutaneously, in particular a prosthetic valve placed on a deployable stent. The implant can also be used to perform an annuloplasty, said actuation means then comprising an abutment integral with the implant and an abutment integral with the catheter; once the implant has been deployed, the abutment integral with the implant meets the abutment integral with the catheter and thus limits the longitudinal progress of the implant without limiting the rotation of said implant; continuing rotation of the implant around its axis after this longitudinal progress limitation causes gathering of the annulus portion in which the implant is placed.

The implant can comprise coils having a uniform pitch. It can also comprise coils having a varied pitch, said pitch being greater at the distal part of the implant and smaller at the proximal part of the implant. During screwing of an implant of this type in the valve annulus, the proximal coils having the smaller pitch contract the portion of the annulus wherein the distal coils having the greater pitch were previously engaged, thereby causing this portion of the annulus to contract and thus performing an annuloplasty.

The aforementioned means for actuating the implant comprises a rod rotationally connected to the implant, this connection being releasable to allow, after placement of the implant, separation of said implant from said rod. This releasable connection may in particular consist of a releasable snap-locking arrangement of the rod and the implant, said arrangement being released through axial tension exerted on the rod so as to separate it from the corresponding end of the implant; this can also be done by unscrewing, or other similar releasable connection means.

Preferably, each guide member is connected to means for its actuation making it possible to rotate the guide member in relation to the catheter.

This rotation makes it possible to ensure that each guide member is indeed engaged along the edge of the valve annulus connected to the wall comprising said annulus.

Preferably, the catheter contains two deployable guide members as previously mentioned, a first of which can be engaged on one side of the valve and the second of which can be engaged on the other side of the valve, and the implant is engaged around these two guide members.

In this way, the implant is guided during its placement by these two guide members, on the two surfaces of the valve annulus.

Preferably, in this case, the guide member, which is found, once deployed, on the other surface of the valve relative to the catheter, may comprise a bearing portion able to bear against the surface of the valve opposite the catheter, making it possible to pinch this tissue between it and the end of the catheter.

This pinching makes it possible to ensure stable positioning of the catheter during deployment of the implant.

This bearing portion may be formed in particular by a distal portion of the guide member, designed to be deployed, which is connected by a bent portion to a proximal portion of the guide member intended to remain in the catheter, said bent portion allowing, after deployment, orientation of said distal portion substantially in the plane of the valve annulus.

This bent portion may in particular be generated by shape memory, then able to be made of "nitinol".

The implant can be placed from the commissure formed by two leaflets adjacent to the treated valve; in this case, when a guide member contained by the catheter must be deployed on the surface of the valve opposite the catheter, this deployment can be done by going through this commissure.

The implant can also be placed outside a commissure of this type, in which case the catheter, or another catheter comprised by the material, includes a piercing needle for the valve annulus. In particular, in this case, the material comprises a first catheter containing said piercing needle, which is hollow; a guidance wire able to be slid through the needle; a second catheter, containing the aforementioned guide member(s) and implant, the guide member intended to extend on the surface of the valve opposite the second catheter being tubular and engaged on the guidance wire.

The first catheter makes it possible to perform the piercing and deploy the guidance wire; said guidance wire is left in place and said first catheter and the needle are removed; the second catheter is then introduced while being guided by the guidance wire; said guidance wire makes it possible to guide the guide member during its deployment.

When the material comprises two guide members each intended to be engaged on one of the surfaces of the valve or the valve annulus, as described above, the guide member intended to be engaged on the surface of the valve opposite the catheter advantageously being tubular and being engaged on this guidance wire.

Positioning of the catheter and engagement of the guide member on the surface of the valve opposite the catheter are thus done under optimal conditions.

According to one particular embodiment of the invention, the material comprises a guide member positioned such that it can be deployed on one side of the catheter diametrically opposite that on which another guide member is deployed.

These diametrically opposed guide members make it possible to ensure perfect positioning of the catheter as close as possible to the valve annulus, without rotating the guide members relative to the catheter, these two diametrically opposed guide members allowing self-shifting of the materials along the wall to which the annulus is connected.

The percutaneous operating method according to the invention comprises steps consisting of using at least one catheter, comprising at least one guide member able to be deployed from said catheter so as to extend along a portion of the valve annulus of the valve, in the immediate vicinity of said valve annulus, and an implant having a helical shape engaged on said guide member, connected, with the possibility of being separated, to actuation means making it possible to move said implant forward while driving it in rotation along its axis; deploying the implant from the catheter by causing said implant to move forward and driving it in rotation along its axis, said rotation allowing the implant to penetrate the tissue of the valve annulus while being guided along said annulus by said guide member.

The implant used may be longitudinally compressible and can adopt an extended introduction form and a shortened form making it possible to reduce the length of the annulus portion in which it is implanted.

The implant used can also have an invariable or slightly variable length, longitudinally.

In this case, the method may comprise a step consisting, after placement of the implant, of percutaneously implanting and anchoring a prosthetic valve.

The implant used may also comprise coils having an inconstant pitch, said pitch being larger at the distal part of the implant and smaller at the proximal part of said implant.

The method according to the invention may also comprise steps consisting of deploying a first guide member and a second guide member, on the surface of the valve facing the catheter and on the surface of the valve opposite the catheter, respectively; positioning the two guide members in relation to each other so as to hold the valve tissue between the guide members.

The method according to the invention may also comprise steps consisting of introducing the catheter at the commissure formed by two leaflets adjacent to the valve, and deploying a deployable member through said commissure.

The method according to the invention may also comprise steps consisting of introducing, outside the commissures formed by the leaflets of the valve, a catheter including a piercing needle for the valve annulus; piercing the valve annulus using said needle; removing the needle and deploying, through the hole made by said needle, a guide member designed to be placed on the side of the valve opposite the catheter.

In this case, the method may in particular comprise steps consisting of piercing said hole using a first catheter containing said needle; introducing, after piercing said hole, a guidance wire through this hole; leaving this guidance wire in place and removing said first catheter as well as the needle; and introducing a second catheter, containing the aforementioned guidance wire(s) and implant, one of the guide members being tubular and engaged on the guidance wire.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

The invention will be well-understood, and other characteristics and advantages thereof will appear, in reference to the appended diagrammatic drawing, illustrating, as non-limiting examples, several possible embodiments of the material it concerns.

FIG. 1 is a partial cross-section of a heart, in which a first catheter is introduced up to the mitral valve.

FIG. 2 is a cross-section of this valve, after piercing of a hole through the valve annulus, and of the first catheter.

DETAILED DESCRIPTION OF THE INVENTION

Figure 3:
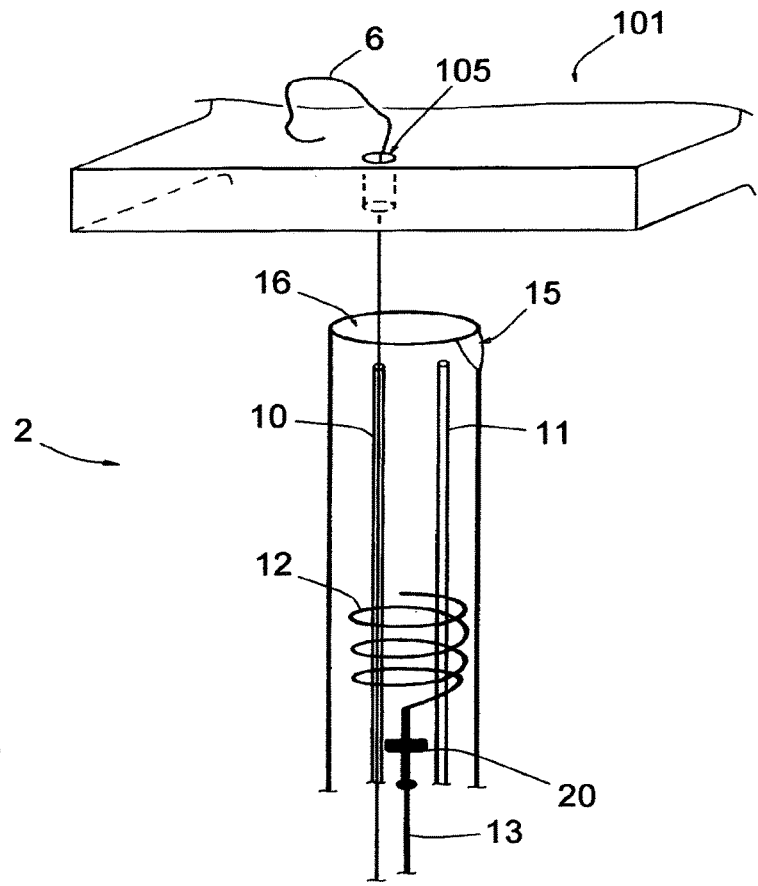
FIGS. 3 to 8 are diagrammatic views of the material according to a first embodiment, and of a portion of the mitral valve, during the various successive steps in placing an implant to treat this valve.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of embodiments hereof are in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

For simplification, the parts or elements of one embodiment which are found identically or similarly in another embodiment will be identified using the same numeric references and will not be described again.

FIGS. 1 to 8 illustrate a material for treating a heart valve, in particular a mitral valve 101 of a heart 100 (cf. FIG. 1), which comprises a first catheter 1, diagrammatically illustrated in FIG. 2, and a second catheter diagrammatically illustrated in any of FIGS. 3 to 12.

As shown in FIG. 1, the first catheter 1 is introduced through the aorta 102, then bears against the heart wall at the ventricle 103 and is directed such that its free end is positioned at the valve 101, immediately below the annulus 104 thereof, as shown by FIG. 2.

Said catheter 1 contains a hollow needle 5 which, once the catheter has been positioned, is slid into the catheter 1 until it goes through the annulus 104. A guidance wire 6 is then slid inside the needle 5 until it goes past the auricular side of the valve 101.

Figure 4:
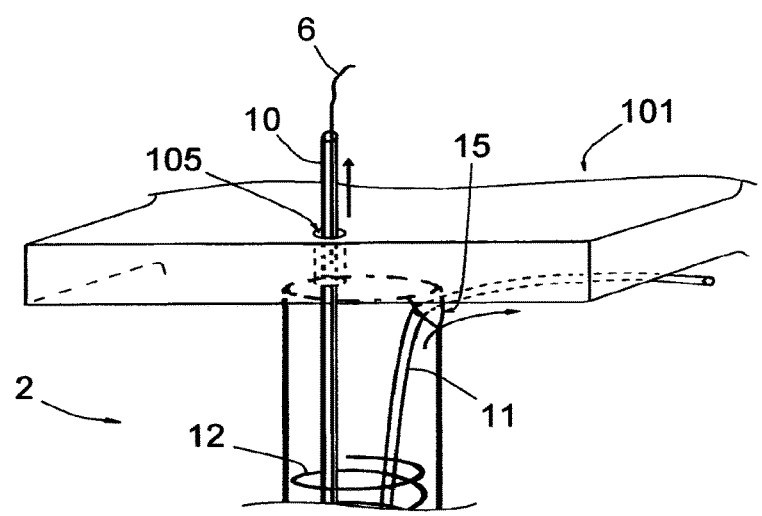

The catheter 1 is then removed from the heart 100, without removing the wire 6, then the catheter 2 is introduced along said wire 6 until it in turn arrives against the valve 101 of the ventricular side (cf. FIGS. 3 and 4).

As shown by these FIGS. 3 and 4, said catheter 2 contains two deployable guide members 10, 11, an implant 12 having a helical shape and an actuating rod 13 connected to one end of the implant 12 with a rotating connection (for clarity of the drawing, the body of the catheter 2 is shown as being transparent).

The guide member 10 is tubular and is engaged on the wire 6, thus making it possible to guide the catheter 2 to the aforementioned position. It appears in FIG. 4 that this guide member 10 is designed to be engaged on the auricular side of the valve 101, through the hole 105 previously made by the needle 5.

The other guide member 11 is not tubular and is engaged in a lateral zone of the catheter 2, leading to the outside through a lateral opening 15 separate from the main end opening 16 of said catheter 2. Said guide member 11 is designed to be engaged on the ventricular side of the valve 101, through said lateral opening 15.

Figure 5:
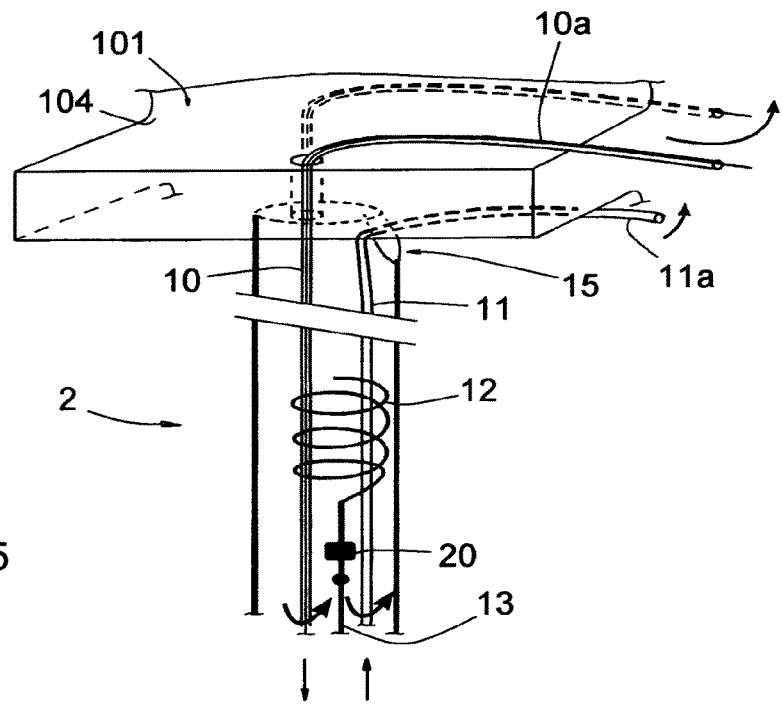

The distal part 10a of the guide member 10 intended to be deployed from the auricular side of the valve 101 is in a shape memory material. As shown in FIG. 5, once deployed, it assumes a bent shape, by shape memory.

Figure 6:
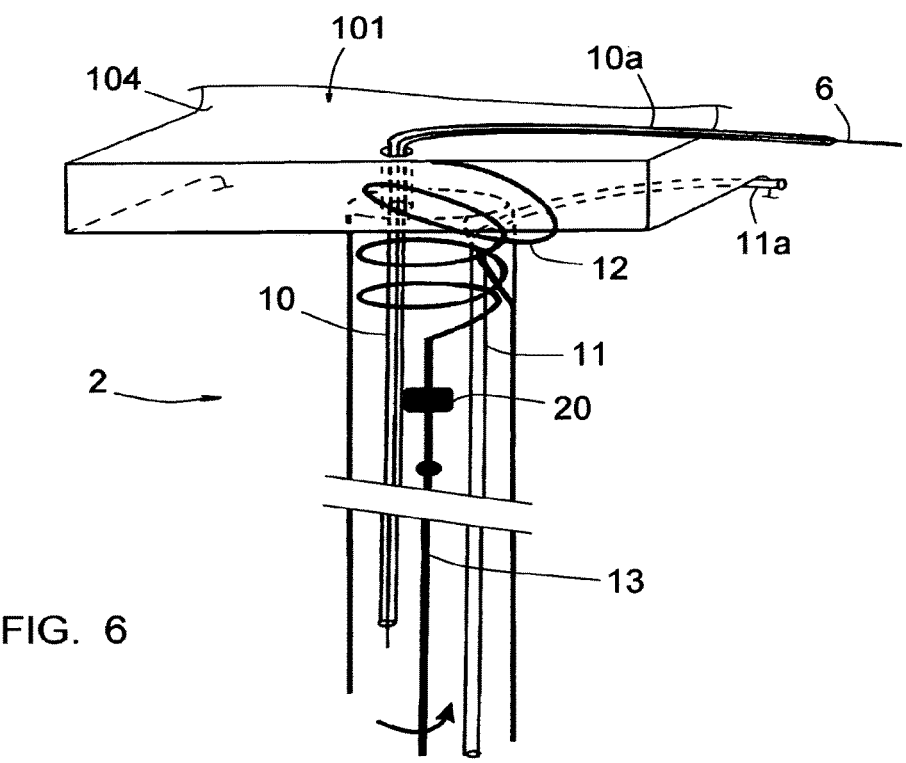

It is shown in this FIG. 5 that the guide members 10 and 11 can be rotated relative to the catheter 2, along the axis of said catheter 2, such that, by this rotational movement, their parts 10a, 11a deployed outside the catheter 2 can be engaged at the bottom of the above-annular and sub-annular groove formed by the annulus 104 of the valve 101. FIG. 5 also shows that the guide member 10 can, once its distal portion 10a has adopted said bent shape, be slid into the catheter 2 in the proximal direction while the guide member 11 is either kept in position or slid in this same catheter 2 in the distal direction. The result, as shown in FIG. 6, is pinching of the valve tissue 101, along the annulus 104, which ensures that the catheter 2 is held perfectly in position.

As shown in FIGS. 3 to 8, the implant 12 is engaged both around the guide member 10 and around the guide member 11. Once the aforementioned immobilization of the catheter 2 has taken place, the implant 12 is moved forward using the rod 13 and is simultaneously driven in rotation in the direction of screwing of its coils. The distal end of this implant 12 is self-tapping, such that the implant 12 penetrates the tissue forming the annulus 104 (cf. FIG. 6).

Figure 7:
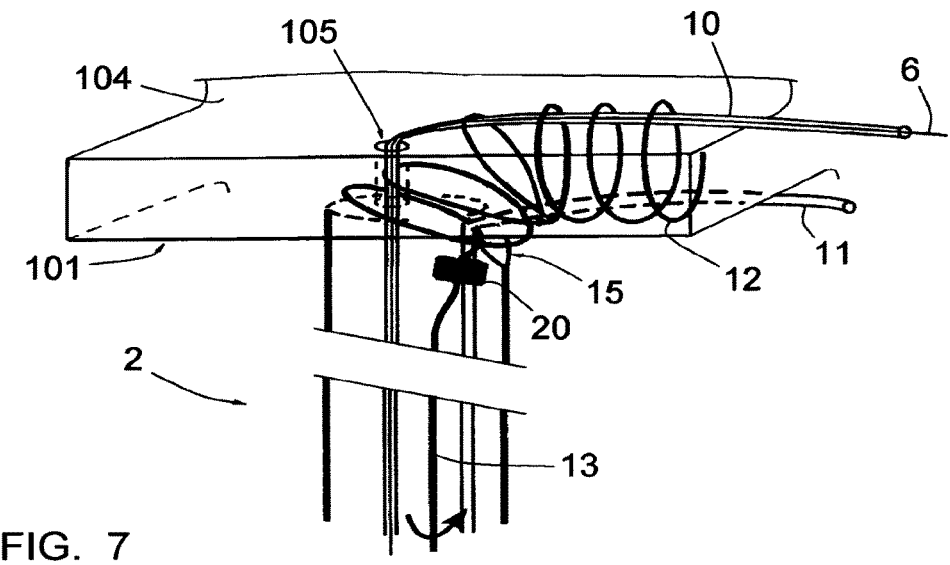

FIG. 7 shows that the implant 12 is thus "screwed" into the tissue of the annulus 104 until an abutment 20 located at the proximal end of the implant 12 meets the tissue of the annulus 104.

The rod 13 is connected to this abutment 20 with separation possibility, for example by a releasable snap-locking arrangement and, once the implant 12 has been completely placed (cf. FIG. 8), suitable tension is exerted on the rod 13 so as to separate it from the abutment 20.

Figure 8:
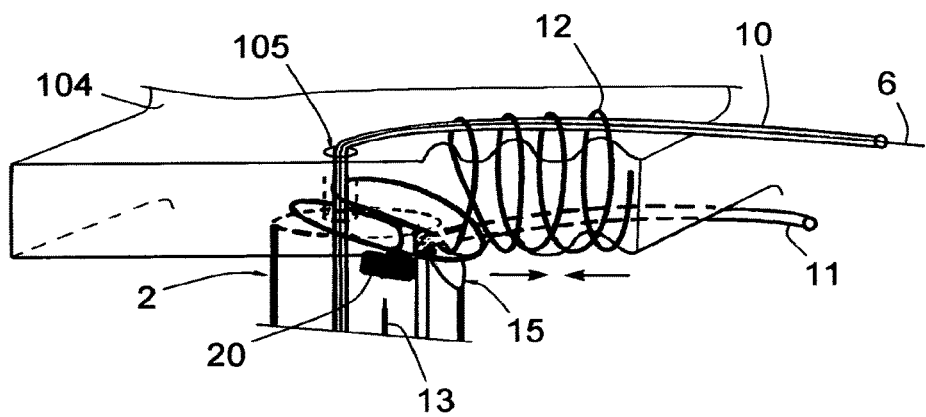

In the embodiment shown in FIGS. 3 to 8, the implant 12 is in a shape memory material and is such that before heating by the patient's organism, it adopts a longitudinally extended shape and once heated by the organism, it contracts longitudinally, the pitch of its coils decreasing, as appears in FIG. 8. This reduction in pitch makes it possible to contract the tissue of the annulus 104, which performs, in whole or in part, an annuloplasty, i.e. a reduction of a distention of the annulus 104.

After placement of the implant 12, the guide members 10 and 11 are removed by sliding, then the catheter 2 is removed, as is the guidance wire 6.

FIGS. 9 to 12 show, very diagrammatically, another embodiment of the material according to the invention, in which the implant 12 has a substantially invariable length. For clarity of the drawing, the guide members 10 and 11 were not illustrated.

In this case, the catheter 2 and the actuating rod 13 comprise respective abutment surfaces 22 and 23, which meet at the end of introduction of the implant 12 in the annulus 104, this meeting blocking the forward motion of the implant 12, but not preventing said implant 12 from being driven in rotation along its axis.

Figure 9:
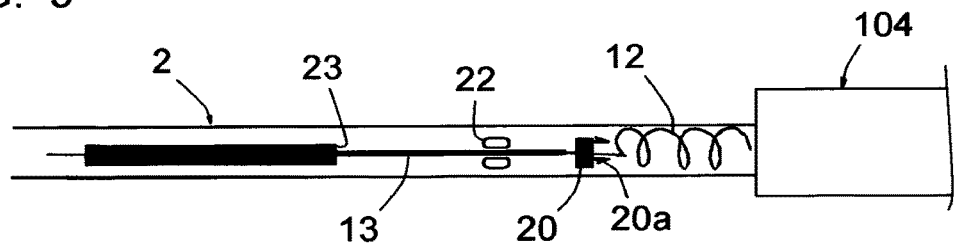
FIGS. 9 to 12 are very simplified diagrammatic views of four steps in placing the implant according to a second embodiment.
Figure 10:
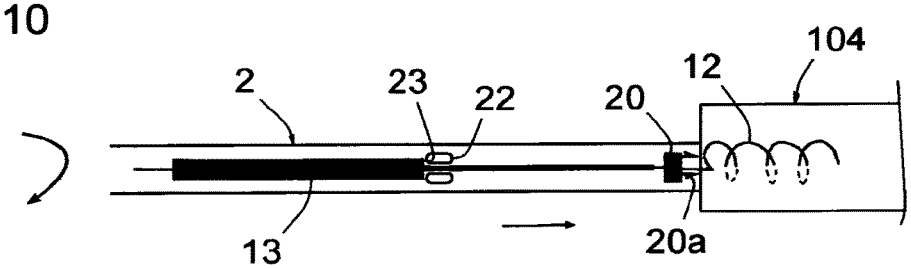
Figure 11:
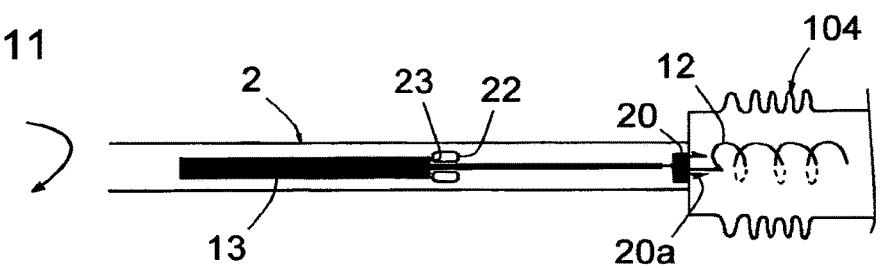

From the position shown in FIG. 9, the implant 12 is introduced into the annulus 104, until the abutment 23 arrives against the abutment 22 (cf. FIG. 10); the abutment 20 is, in this embodiment, equipped with anchors 20a able to penetrate the tissue of the annulus 104 and, in this same position, these anchors 20a are found near the wall of the annulus 104, but without penetrating said wall.

Rotation of the implant 12 along its axis is then continued, which, in light of the longitudinal immobilization of said implant 12, causes movement, in the proximal direction of the catheter 2, of portions of the annulus 104 gone through by the respective coils of the implant 12. This movement makes it possible to compress the tissue forming said annulus 104 and, simultaneously, to cause the anchors 20a to penetrate the wall of this tissue, ensuring the immobilization of the implant 12 in rotation (cf. FIG. 11).

Figure 12:
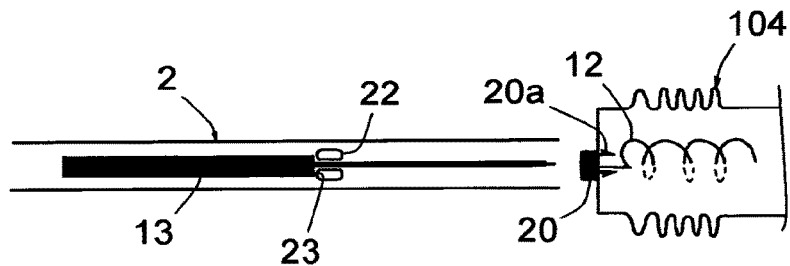

The abutment 20 can then be separated from the rod 13, as previously described (cf. FIG. 12).

Figure 13:
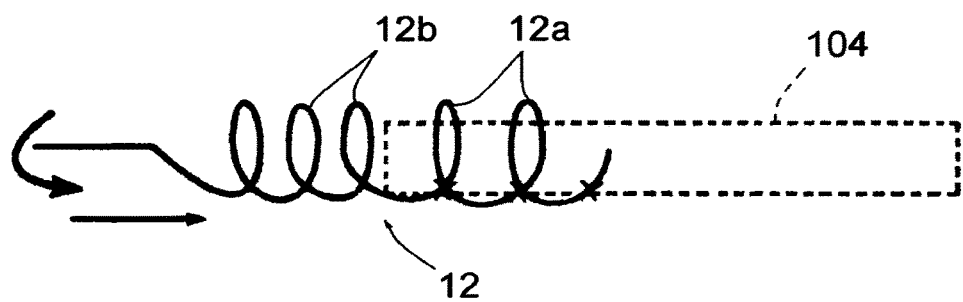
FIGS. 13 and 14 are principle views of two steps in placing an implant according to another embodiment.
Figure 14:
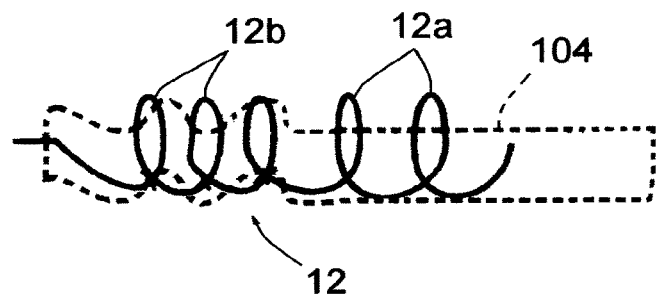

FIGS. 13 and 14 show a third embodiment of the material according to the invention, in which the implant 12 comprises coils having an inconsistent pitch, this pitch being larger at the coils 12a located in the distal part of the implant 12 and smaller at the coils 12b located in the proximal part of this implant.

As can be understood from comparing FIGS. 13 and 14, during screwing of the implant 12 into the annulus 104, the proximal coils 12b having the smaller pitch contract the portion of the annulus 104 wherein the distal coils having the larger pitch were previously engaged, thereby causing this portion of the annulus 104 to contract and thus performing an annuloplasty.

Figure 15:
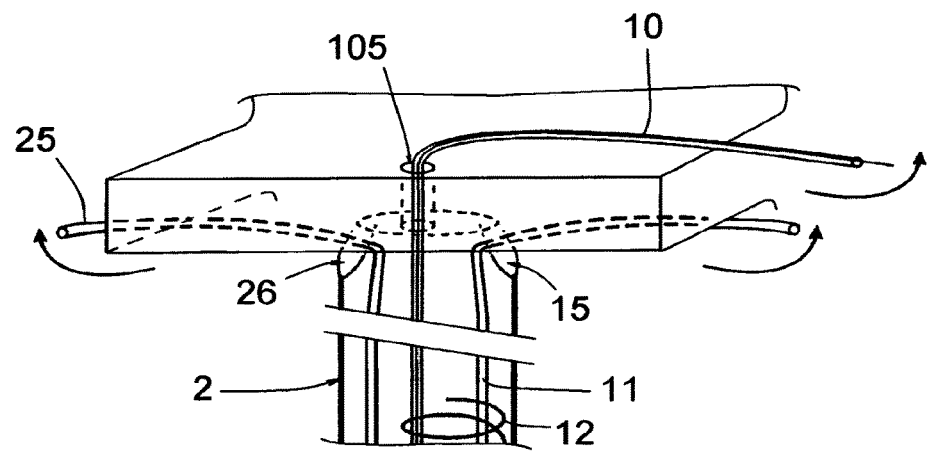
FIGS. 15 and 16 are very simplified diagrammatic views, perspective and top views, respectively, of the material according to yet another embodiment.
Figure 16:
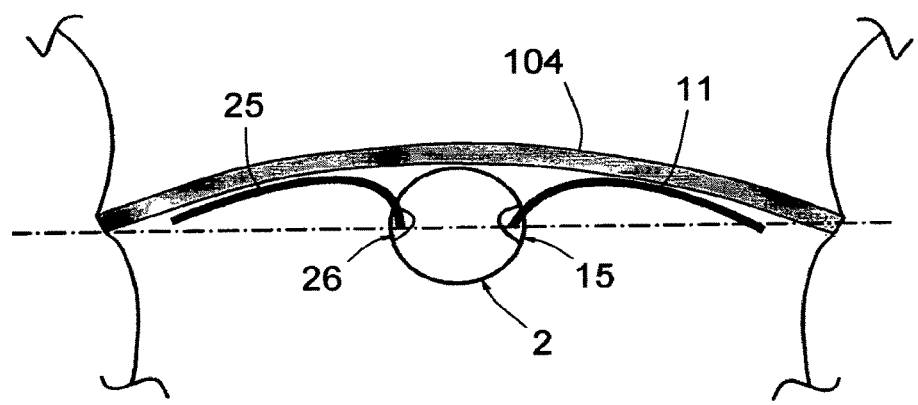

FIGS. 15 and 16 show a variation of an embodiment of the material, in which the catheter 2 comprises, in addition to the guide members 10 and 11, a third guide member 25, diametrically opposite the guide member 11. This guide member 25 can be deployed through an opening 26 of said catheter 2 diametrically opposite the opening 15.

These two guide members 11, 25 make it possible to ensure perfect positioning of the catheter 2 as close as possible to the annulus 104, as shown in FIG. 16.

As appears from the preceding, the invention provides a material for treating a heart valve, in particular a mitral valve of a heart, that is fully satisfactory and makes it possible to conduct either annuloplasties or reinforcements of the valve annulus under optimal conditions.

It goes without saying that the invention is not limited to the embodiment described above as an example, but that it extends to all forms of embodiments covered by the appended claims.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An apparatus for treating a heart valve, comprising:
   a catheter configured for percutaneous introduction through a minimally invasive vascular access;
   a guide member deployable from a distal end of the catheter, the guide member having a distal portion of a length that is configured to extend from the distal end of the catheter such that when the guide member is deployed for treating the heart valve the distal portion of the guide member extends from a proximal side to a distal side of a valve annulus and a bent shape of the distal portion of the guide member is configured to engage the distal side of the valve annulus; and
   an implant having a helical shape and being disposed within the catheter being spiraled around the guide member, and being rotatable relative to the guide member, the implant being detachably connected to an actuator that is disposed within the catheter, the actuator being configured to rotate the implant about the guide member and to distally advance the implant relative to the guide member,
   wherein the implant is configured to be deployed from the distal end of the catheter and to penetrate the tissue of the valve annulus while longitudinally advancing along and rotating relative to the deployed distal portion of the guide member.

2. The apparatus according to claim 1, wherein the implant is configured to have a longitudinally extended form when advanced into a portion of the valve annulus and is configured to assume a shortened form when implanted into the portion of the valve annulus to reduce a length of the valve annulus portion.

3. The apparatus according to claim 2, wherein the implant is made of a shape memory material.

4. The apparatus according to claim 1, wherein the implant has an invariable or slightly variable length.

5. The apparatus according to claim 4, wherein the catheter includes a first abutment surface at the distal end thereof and the actuator includes a second abutment surface disposed proximal of the implant, such that the first and second abutment surfaces meet when the entire implant is advanced into a portion of the valve annulus.

6. The apparatus according to claim 5, wherein when the first abutment surface meets the second abutment surface longitudinal advancement of the implant is restricted while rotation of the implant is unimpeded.

7. The apparatus according to claim 6, wherein when the first abutment surface meets the second abutment surface and further rotation of the implant occurs the implant is configured to compress the valve annulus portion within which it is deployed.

8. The apparatus according to claim 1, wherein the helical shape of the implant comprises coils having a uniform pitch.

9. The apparatus according to claim 1, wherein the guide member is configured to rotate relative to the catheter.

10. The apparatus according to claim 1, wherein the distal portion of the guide member includes a bearing portion configured to bear against the distal side of the valve annulus opposite the catheter, making it possible to pinch the valve annulus between the bearing portion and the distal end of the catheter.

11. The apparatus according to claim 10, wherein the bearing portion of the guide member is connected by a bent portion of the distal portion to a proximal portion of the guide member, the proximal portion being configured to remain in the catheter after deployment.

12. The apparatus according to claim 11, wherein after deployment of the distal portion of the guide member from the distal end of the catheter, the bent portion is configured to orient the distal portion substantially in a plane parallel with the distal side of the valve annulus.

13. An apparatus for treating a heart valve, comprising:
a catheter configured for percutaneous introduction through a minimally invasive vascular access;
a guide member deployable from a distal end of the catheter, the guide member having a distal portion of a length that is configured to extend from the distal end of the catheter such that when the guide member is deployed for treating the heart valve the distal portion of the guide member extends from a proximal side to a distal side of a valve annulus and a bent shape of the distal portion of the guide member is configured to engage the distal side of the valve annulus; and
an implant disposed within the catheter to wrap around the guide member and being rotatable relative to the guide member, the implant being detachably connected to an actuator that is disposed within the catheter, the actuator being configured to rotate the implant about the guide member and to distally advance the implant relative to the guide member,
wherein the implant is configured to be deployed from the distal end of the catheter and to penetrate the tissue of the valve annulus while longitudinally advancing along and rotating relative to the deployed distal portion of the guide member.

14. The apparatus according to claim 13, wherein the implant comprises coils having a uniform pitch.

15. The apparatus according to claim 13, wherein the implant has an invariable or slightly variable length.

16. The apparatus according to claim 15, wherein the catheter includes a first abutment surface at the distal end thereof and the actuator includes a second abutment surface disposed proximal of the implant, such that the first and second abutment surfaces meet when the entire implant is advanced into a portion of the valve annulus.

17. The apparatus according to claim 16, wherein when the first abutment surface meets the second abutment surface longitudinal advancement of the implant is restricted while rotation of the implant is unimpeded.

18. The apparatus according to claim 17, wherein when the first abutment surface meets the second abutment surface and further rotation of the implant occurs the implant is configured to compress the valve annulus portion within which it is deployed.

19. The apparatus according to claim 13, further comprising:
a second guide member having a distal portion configured to engage the proximal side of the valve annulus when deployed from the distal end of the catheter.

20. The apparatus according to claim 19, wherein when the implant is deployed from the distal end of the catheter to penetrate the tissue of the valve annulus, the implant is configured to be longitudinally advanced along and rotated relative to each of the deployed distal portions of the guide members, and
wherein the implant remains engaged with and rotates around both of the deployed distal portions of the guide members during advancement of the implant from the distal end of the catheter.

* * * * *